United States Patent
Vladyka, Jr. et al.

(10) Patent No.: US 6,858,725 B1
(45) Date of Patent: Feb. 22, 2005

(54) MICROCRYSTALLINE CELLULOSE CUSHIONING GRANULES

(75) Inventors: Ronald S. Vladyka, Jr., Somerset, NJ (US); David F. Erkoboni, Pennington, NJ (US); Christopher A. Sweriduk, Chalfont, PA (US)

(73) Assignee: R.P. Scherer Technologies, Inc., Paradise Valley, NV (US)

( * ) Notice: Subject to any disclaimer, the term of this patent is extended or adjusted under 35 U.S.C. 154(b) by 427 days.

(21) Appl. No.: 09/708,581

(22) Filed: Nov. 9, 2000

(51) Int. Cl.$^7$ .............. C08B 37/00; C07H 1/00; A61K 31/715; A61K 9/16; A61K 9/20
(52) U.S. Cl. .............. 536/56; 536/124; 514/54; 514/57; 424/457; 424/458; 424/465; 424/489; 424/490; 424/494; 424/496
(58) Field of Search .......... 536/56, 124; 424/489, 424/490, 494, 496, 457, 458, 465; 514/57, 54

(56) References Cited

U.S. PATENT DOCUMENTS

| | | | |
|---|---|---|---|
| 4,837,030 A | | 6/1989 | Valorose, Jr. et al. |
| 4,867,985 A | | 9/1989 | Heafield et al. |
| 5,384,130 A | * | 1/1995 | Kamada .............. 424/461 |
| 5,607,695 A | | 3/1997 | Ek et al. .............. 424/468 |
| 5,725,886 A | | 3/1998 | Erkoboni et al. |
| 5,780,055 A | | 7/1998 | Habib et al. |
| 6,117,451 A | * | 9/2000 | Kumar .............. 424/465 |
| 6,123,964 A | * | 9/2000 | Asgharnejad et al. ....... 424/489 |
| 6,149,943 A | * | 11/2000 | McTeigue et al. .......... 424/494 |
| 6,384,020 B1 | * | 5/2002 | Flanner et al. .............. 514/53 |

FOREIGN PATENT DOCUMENTS

| | | |
|---|---|---|
| JP | 61-213201 | 9/1986 |
| WO | WO 91/18590 | 12/1991 |
| WO | WO 97/10810 | 3/1997 |

OTHER PUBLICATIONS

CRC Handbook of Chemistry and Physics, Editor Robert C. Weast, Ph.D., 60$^{th}$ Edition, Chemical Rubber Publishing Company, 2$^{nd}$ printing, 1980, p. D–21, Compound No. 411.*
International Search Report for the corresponding PCT application, PCT/US00/31015.

* cited by examiner

*Primary Examiner*—James O. Wilson
*Assistant Examiner*—Everett White
(74) *Attorney, Agent, or Firm*—Knoble Yoshida & Dunleavy, LLC

(57) ABSTRACT

Granulation of microcrystalline cellulose with a granulating fluid consisting of water and a water-miscible, volatile, polar organic solvent yields porous granules which are comprised of particles that are larger than the ungranulated microcrystalline cellulose. This granulated microcrystalline cellulose is capable of cushioning controlled release particles and barrier coated particles from the compression forces used in tableting, thereby maintaining the physical integrity of the components of the tablet.

26 Claims, No Drawings

US 6,858,725 B1

MICROCRYSTALLINE CELLULOSE CUSHIONING GRANULES

BACKGROUND OF THE INVENTION

1. Field of the Invention

This invention relates to tablet excipients that provide a cushioning effect for preserving the physical integrity of other components of the tablet. More specifically, the invention relates to granules including porous microcrystalline cellulose that cushion controlled release particles during tableting, tablets containing such porous microcrystalline cellulose granules and methods for making such granules and tablets.

2. Description of the Prior Art

Controlled release particles containing an active ingredient for pharmaceutical or veterinary products have been employed in a variety of different delivery forms, such as sprinkles or capsules. For various reasons, it has become desirable to incorporate such controlled release particles into tablets made using a compression step to form the tablet. However, such controlled release particles are relatively fragile and thus may become damaged during the compression step of tableting thereby significantly altering the release rate of the active ingredients from the controlled release particles. There are some commercial products that contain controlled release particles in a tablet form. For example, Theo-dur® is a tablet form of controlled release particles of theophylline contained in a wax matrix. Also, the popular drug Prilosec® is sold in the form of tablets that include controlled release particles therein.

Currently, microcrystalline cellulose ("MCC"), for example, Avicel® PH grades, is widely utilized in the preparation of pharmaceutical and veterinary tablets, primarily as a compression aid and binder, and, secondarily, as a disintegrant. Different grades of MCC provide different degrees of compressibility, but none is capable of sufficiently protecting the physical integrity of other components in the tablet, particularly controlled release particles, granules, or spheres during the compression step of tableting. The damage that occurs to such controlled release particles during the compression step of the tableting process may be measured by the increased rate at which the active ingredient is released from the tablet after compression as compared to the release rate for the controlled release particles prior to compression. It is believed that one factor which may contribute to the increased release rate is that the fragile, controlled release coating on the outer surface of the controlled release particles can crack during the compression step of the tableting process.

SUMMARY OF THE INVENTION

In a first aspect, the present invention relates to a process for the granulation of MCC to provide a tableting excipient with improved cushioning properties. Granulation of MCC with a granulating fluid containing a polar organic solvent followed by removal of the polar organic solvent yields porous MCC granules that provide enhanced cushioning during the compression step of a tableting operation. This cushioning effect is sufficient to eliminate or significantly reduce the damage to controlled release particles that has been observed during the compression step of a tableting operation with ungranulated MCC, MCC granulated with an aqueous solvent and with other conventional tableting excipients. Substantially all of the polar organic solvent component of the granulating fluid is removed from the MCC granules by controlled drying in order to preserve the density of the MCC granules.

In a second aspect, the present invention relates to granules containing MCC and having a density and mean particle size sufficient to provide cushioning of controlled release particles during the compression step of a tableting operation. Such granules may be made using the granulation process of the invention described above. The granules containing MCC may optionally be provided with a coating or outer layer of a hydrocolloid in order to further enhance their cushioning properties and compression properties.

In a third aspect, the present invention relates to pharmaceutical and veterinary tablets which include controlled release particles and granulates containing MCC according to the present invention. Such tablets have the advantage that they can be made using existing tableting operations and still provide the desired release rates for the active ingredient contained in the controlled release particles.

DETAILED DESCRIPTION OF THE INVENTION

MCC is a common excipient for pharmaceutical and veterinary tablets. It is a purified, partially depolymerized cellulose that is produced by treating a source of cellulose, preferably alpha cellulose in the form of a pulp from fibrous plants, with a mineral acid, such as hydrochloric acid. The acid selectively attacks the less ordered regions of the cellulose polymer chain, thereby exposing and freeing the crystallite sites, thereby forming the crystallite aggregates that constitute MCC. The aggregates are then separated from the reaction mixture and washed to remove degraded by-products. The resulting wet mass, generally containing 40 to 60 percent moisture, is referred to in the art by several names, including hydrolyzed cellulose, MCC, microcrystalline cellulose wet cake, or simply wet cake. It is this hydrolyzed cellulose, which may be further modified, for example, by attrition or spray drying, that is utilized as the starting material for the granulation process of the present invention.

If a spray drying operation is employed, aggregates of the individual MCC-containing crystallites are formed. The spray-dried, unattrited material is sold commercially as a powder in grades having different average particle sizes ranging from about 20 microns to 190 microns. Typical of commercially available MCC are the materials sold by FMC Corporation as Avicel® PH grades.

A process known as steam explosion may also be used to produce MCC. In this process wood chips are placed in a chamber into which super-heated steam is introduced. After being maintained in contact with the super-heated steam for period of about 1–5 minutes, an exit valve for the chamber is opened rapidly, releasing the contents explosively and yielding MCC. Although no additional acid is introduced into the reaction mixture, the acidic materials in the wood chips and the elevated temperature and pressure serve to hydrolyze the cellulose and degrade it.

Regardless of the average particle size of the particular Avicel® PH grade which is being used as an excipient to improve compressibility of a tablet, none of the materials as they are now sold provides sufficient protection to substantially preserve the physical integrity of other components of a tablet formulation during the compression step of tableting. Components desirable for incorporation into tablets for which the physical integrity of the component must be substantially preserved, include controlled release particles such as sustained release particles, enteric release release particles including those which release at intestinal and colonic pH, osmotic release particles and taste-mask particles, as well as barrier coated particles, among others. The present invention can be applied to preserve the physical integrity of many different components of tablets during the compression step of tableting. For the purpose of illustration only, the present invention will be described in greater detail with reference to protecting the physical integrity of sustained release particles.

As previously stated, during tableting the forces required to compress the formulation into a tablet generally cause damage to controlled release particles contained in the tablet formulation, thereby greatly increasing the rate at which the active ingredient is released. It has now been found that the cushioning effect of commercially available forms of MCC, for example, Avicel® PH-101 (average particle size 50 microns) can be greatly enhanced by granulating the MCC with a granulating fluid which contains a polar organic solvent. The granulation process creates MCC granules that are both larger than the original ungranulated MCC particles and, more importantly, are better able to cushion controlled release particles during the compression step of a tableting operation.

It is well known that increasing the particle size of MCC by granulation using water as the granulation solvent generally results in both an increased density and a decreased compressibility of the resultant MCC granules, as compared to ungranulated forms of MCC. Unexpectedly, the MCC granules of the present invention typically have a lower density than MCC granules made using water as the granulation solvent. The lower density of the MCC granules of the present invention provide a cushioning effect that is capable of at least significantly reducing the damage which would otherwise be observed as a result of the compression of controlled release particles during a tableting operation when other, conventional tableting excipients are employed.

The process of the present invention to produce MCC granules can begin with commercially available forms of MCC, for example, Avicel® PH-101 or its precursor wet cake, or MCC that is produced by hydrolysis or steam explosiion. In addition to the MCC that is produced by either acid hydrolysis or steam explosion, other forms of cellulose including micro reticulated MCC, and hydrolyzed cellulose wet cake, for example, a product sold under the trademark Solka-Floc®, may also be used to prepare the novel granules which are capable of providing this cushioning effect. If the form of cellulose used contains water, the water content of the granulating fluid must be adjusted to compensate since the water contained in the cellulose will function as a portion of the granulating fluid.

A mixture of the MCC and the granulating fluid is prepared. The granulating fluid contains a mixture of water and a volatile, water-miscible, polar organic solvent. The ratio of the weight of granulating fluid to the weight of MCC may vary from about 1:2 to about 2:1, more preferably from about 3:4 to about 1.5:1. Higher amounts of granulating fluid would generally result in over-wetting and require longer times to evaporate the granulating fluid and might also result in an intractable product which may have to be milled after it has been dried. Lower amounts of granulating fluid may not be sufficient to achieve the porous, cushioning structure that is required to protect the controlled release particles from damage. The volume ratio of water to the polar organic solvent in the granulating fluid may range from about 85:15 to about 15:85, more preferably from about 70:30 to about 30:70.

The granulation may be carried out in any suitable granulating apparatus including both a low shear granulating apparatus and a high-shear granulating apparatus. The granulation mixture is mixed for a period that is sufficient for the MCC to be substantially completely and evenly moistened with the granulating fluid and to develop the particle size of the MCC granules to the desired particle size ranges and distribution. Generally, the mixing time will depend, to some extent on the type of granulating apparatus employed. Over-mixing and over-wetting are generally undesirable since this may, in some cases, result in an increased density of the dried granulate and, concomitantly, a reduction in the effectiveness of cushioning property of the MCC granules.

Mixing must therefore be adjusted to result in a final MCC product having the desired characteristics. Thus, mixing step should be shortened if the density of the final, dried material begins to increase significantly. More preferably, mixing is carried out until MCC granules are produced which have particle sizes similar to the particle size range of the controlled release particles and density is not significantly increased relative to the ungranulated MCC.

At the conclusion of the period of mixing, the wet MCC granules can be forced through a screen that may vary from a screen size of about 12 mesh (1680 microns) to about 18 mesh (1000 microns). The mesh size of the screen is not of great significance in relation to the compression performance of the MCC granules. Therefore, screens having both larger and smaller mesh sizes are also believed to be useful in this process. As a result of passing through the screen, the MCC granules break up into smaller granules that are then dried. Drying is preferably carried out in a manner that does not significantly increase the density or alter the particle size and therefore reduce the cushioning property of the dried, MCC granules. The use of certain types of granulation techniques may eliminate the need for wet screening of the MCC granules.

The preferred method of drying is controlled drying. Controlled drying is the removal of substantially all of the water-miscible polar organic solvent component of the granulating fluid from the MCC granules at a controlled rate. Preferably, at least 50% of the water-miscible polar organic solvent is removed by controlled drying, and, more preferably at least 60–80% of the water-miscible polar organic solvent is removed by controlled drying. More specifically, the rate of the controlled drying step is controlled by carrying out the drying step with no more than a minimal input of heat or reduction in pressure for drying. Controlled drying may be carried out in drying trays without employing an external source of heat and/or reduced pressure or by use of a fluid-bed dryer. When all, or nearly all, of the polar organic solvent has been removed, the remaining granulating fluid may be removed using elevated temperatures and/or reduction in pressure in an oven, a fluid-bed dryer, or by using any other suitable method of drying. The dried MCC granules may have a water content of up to about 15% by weight, and more preferably up to about 8% by weight, based on the weight of the MCC granules.

Drying too rapidly when significant amounts of the polar organic solvent are still present in the MCC granules may accelerate the removal of the polar organic solvent, leaving water, which may promote excessive hydrogen bonding within the MCC granules. Hydrogen bonding within the aggregates generally leads to denser, less porous granules which may not provide as much cushioning as comparable MCC granules which were dried more slowly. Also, it is generally unnecessary to freeze the water component of the granulating fluid during the drying process.

Suitable, polar, water-miscible, organic solvents which may be used as a component of the granulating fluid include methanol, ethanol, propanol, isopropanol, t-butyl alcohol and acetone. Of these, isopropanol is preferred. Based on the performance of various MCC granules in tablets, there is a minimum amount of the polar organic solvent that must be present during granulation to produce an MCC granule that can provide effective cushioning during tableting. The volume ratio of water to polar organic solvent in the granulating fluid can be from about 15:85 to 85:15. The larger the water content of the granulating fluid, the less granulating fluid that will be required. If more granulating fluid is required, a larger polar organic solvent content of the granulating fluid may be employed. Thus, it is possible to use a volume ratio of, for example 30:70 water to polar organic solvent, provided sufficient granulating fluid, for example, 1.4 times the weight of the MCC being granulated, is used. The same degree of cushioning can be produced by using equal weights of MCC and granulating fluid (i.e. a 1:1 ratio) that is comprised of a volume ratio of 70:30 water to polar organic solvent.

The dried, porous MCC granules of this invention may be incorporated into formulations to be tableted. As exemplified herein, formulations comprising the MCC granules, controlled release particles containing theophylline, and colloidal silicon dioxide are tableted. In commercial applications, additional additives which may be useful in these tablet formulations include binders, disintegrants, antiadherents, surfactants, flow aids, sweeteners and flavoring agents, lubricants and the like, as known by those skilled in the art.

As produced in this process, the particle size of the MCC granules can be distributed over a wide range, typically including particles smaller than about 100 microns to particles larger than 2000 microns. More preferably, the MCC granules have particle sizes distributed over a range of about 150 to 1500 microns and even more preferably 250–1250 microns.

Generally, the MCC granules will have particle sizes which form a substantially Gaussian particle size distribution containing particles having sizes varying over a relatively wide range. Thus, the MCC granules preferably will have a mean particle size of 200–1500 microns, more preferably the mean particle size is from 250–1000 microns and most preferably the mean particle size is from 400–900 microns. The MCC granules are of irregular shape and a wide particle size distribution which promotes packing in tablets made with the MCC granules. Since the irregular shape of the MCC granules, as well as their wide particle size distribution are advantageous for the present invention, further processing of the MCC granules by, for example, extrusion or spheronization is generally undesirable and thus should be avoided.

In order to provide tablets having the greatest uniformity, the materials to be included in the tablets should have similar mean particle sizes. For this reason, a separation of various particles based on pre-selected size ranges, for example, by screening, may be either desirable or necessary after the MCC granules are dried. In this way the sizes of controlled release particles and dried MCC granules can be more closely matched to provide tablets having the greatest uniformity.

The MCC granules of the present invention preferably have a loose bulk density of about 0.2–0.4 g/cc, and more preferably have a loose bulk density of about 0.25–0.35 g/cc. MCC granules with particle sizes near the lower end of the particle size ranges given above will generally have bulk densities at the higher end of the range. MCC granules with particle sizes near the upper end of the particle size ranges given above will generally have bulk densities at the lower end of the range.

In an alternative embodiment of the invention, the MCC granules have a coating or outer layer of a hydrocolloid applied thereto to provide MCC granules containing the hydrocolloid. The weight ratio of the MCC to the hydrocolloid in the dried granule is from about 99:1 to about 70:30 and more preferably from about 90:10 to about 80:20. The addition of the hydrocolloid can enhance the cushioning effect and compressability of the MCC granules of the present invention.

Hydrocolloids suitable for the purpose of the invention may be selected from a variety of hydrophilic, pharmaceutically acceptable polymers capable of forming an aqueous solution or dispersion. These are known, conventional materials examples of which include methylcellulose, sodium carboxymethylcellulose, hydroxypropyl cellulose, hydroxypropyl methylcellulose, gelatin, water soluble cellulose acetate, polyvinyl pyrrolidone, starches, alginates, carrageenan, alginic acid, seed extracts such as locust bean and guar, and tragacanth, arabic and karoya gums. The preferred hydrocolloids for use in the present invention are methylcellulose, hydroxypropyl cellulose, hydroxypropyl methylcellulose and polyvinyl pyrrolidone. The most preferred hydrocolloid is polyvinyl pyrrolidone.

To prepare the MCC granules containing a hydrocolloid, a solution or dispersion of the hydrocolloid is first prepared. The solution or dispersion is then sprayed onto the surface of the MCC granules of the invention to provide hydrocolloid-coated MCC granules. Alternatively, the hydrocolloid may be dry blended with the MCC granules and the blend is then lightly dampened to cause the hydrocolloid to adhere to the outer surface of the MCC granules and dried. Both processes are preferably carried out in a fluidized bed to promote the uniform application of hydrocolloid to the MCC granules. Optionally, the MCC granules with a surface coating or outer layer of hydrocolloid may optionally be conditioned, for example, at 85% relative humidity.

If the MCC granules containing hydrocolloid are fabricated in one process beginning with commercialy available MCC, the hydrocolloid may be added at various times during the process for making the MCC granules. Preferably, the hydrocolloid is added after the MCC granules are completely dried. However, it is also possible to co-process the hydrocolloid and MCC granules by adding the hydrocolloid prior to the drying step which removes the polar organic solvent component of the granulating fluid or prior to the drying step which removes a substantial portion of the water component of the granulating fluid.

The MCC granules and hydrocolloid-containing MCC granules may be used alone or in mixtures having varying proportions of the two types of MCC granules. All of these various forms of MCC granules of this invention are useful with all types of controlled release particles that contain active ingredients. The MCC granules provide the cushioning necessary to maintain a large percentage of these controlled release particles substantially intact such that their release rates are not substantially altered by the compression step of the tableting process. The selection of the particular active ingredient is immaterial to the cushioning effect of the MCC granules, making it possible to tablet a wide variety of active ingredients using the various aspects of the present invention.

Suitable controlled release particles generally contain up to about 75% by weight of active ingredient, based on the total weight of the controlled release particle. It is desirable to make tablets having a high percentage of active ingredient. Thus, the tablets will contain from about 20–80% by weight of the controlled release particles. More preferably, the tablets will contain about 30–60% by weight of the controlled release particles and most preferably about 35–50% by weight of the controlled release particles.

Tablets will also generally contain from about 5–80% by weight of the MCC granules, more preferably about 10–50% by weight, and most preferably about 15–30% by weight of the MCC granules, based on the total weight of the tablet. More preferred tablets typically contain: active ingredient formulated with excipients which can include coatings to form controlled release particles; dry binders and/or compression aids such as the MCC granules of the present invention; and other excipients in amounts of up to about 20% by weight. The other excipients may include a disintegrant in an amount of 0–10% by weight, more preferably 0–5% by weight, and most preferably 0–2% by weight, based on the total weight of the tablet, and one or more lubricants. Conventional lubricants such as magnesium stearate, stearic acid and hydrogenated vegetable oil may be employed in conventional amounts of about 0.1–10% by weight, based on the total weight of the tablet to prevent or inhibit the tablets from sticking to the apparatus used to compress the materials into a tablet.

Other excipients may also include conventional glidants which are employed to improve the flowability of the powders to facilitate handling of the materials during the tableting operation. Typical glidants include talc, and silicas such as fumed silica and precipitated silica.

Friability is one important property of tablets in which the MCC granules of the present invention are incorporated as an excipient. A high percentage of friability reflects the inability of the tablets to survive abrasive forces, making the tablets unsatisfactory as a dosage form. In many cases, the MCC granules which provide the greatest cushioning for controlled release particles also exhibit a high friability. Consequently, it is important to balance friability and hardness to obtain the most useful tablets.

Friability and hardness correlate rather closely with the compression force employed to produce the tablets. Tablets in which MCC granules are a component that have a hardness near or above 4 Kiloponds (Kp) usually have friability below about 3%; and more preferably, below about 2%. The selection of compression forces during tableting is a variable that one skilled in the art of tableting can manipulate to form satisfactory tablets that have the desired sustained release properties, hardness, and friability.

Tablets made using the MCC granules of the present invention preferably are suitable for the application of an additional coating, have relatively smooth, even surfaces, and are free of voids and pores large enough to be visible with the naked eye. The tablets should also be substantially uniform throughout and preferably contain a high percentage of the active ingredient relative to the remainder of the tablet.

The acceptability of tablets made using the MCC granules of the present invention and controlled release particles can be determined from the hardness, friability and the release rate of the active ingredient from the tablet. Release rates are directly related to the amount of damage caused to the controlled release particles during the compression step of tableting. Thus, acceptable tablets will have release rates comparable to or not significantly greater than the release rates of the controlled release particles themselves. Acceptable release rates for particular tablets will depend upon a number of factors familiar to the person skilled in the art including desired dosage, dosing frequency, amount of active ingredient in the tablet, etc.

The following examples are not intended to be limiting as to the type of controlled release particles and/or active ingredients that can be protected during tableting by this novel granulated form of MCC. All examples utilize theophylline which is sustained release-coated with 14% by weight Eudragit® coatings to form the controlled release articles.

EXAMPLE 1

Hydrolyzed cellulose wet cake (400 grams) consisting of 38–42% hydrolyzed cellulose and 58–62% water was slurried in 1000 ml of isopropyl alcohol with 0.5 hour of mixing. This slurry was filtered using vacuum, and the filter cake was again slurried in 1000 ml of isopropyl alcohol. This slurry was mixed for 15 minutes, and then was filtered using vacuum. The wet filter cake was forced through an 18 mesh (1000 micron) screen. The screened, wet, granular material was placed in a pan and dried under vacuum at ambient temperature for about 16 hours. A vacuum oven was then heated to 80° C. When this temperature was attained, the power to the oven was turned off; the partially dried granules were placed in the oven; and the vacuum was restored. The granules remained in the oven until it had cooled to ambient temperature. A dry mixture of 60 parts of the MCC granules and 40 parts of the Eudragit®-coated theophylline was tableted by dry blending and compression, producing tablets weighing 833.1 mg and containing 244.9 mg of theophylline. The results of testing these tablets using a USP apparatus 2 at 50 rpm in 900 ml of 0.1 N hydrochloric acid showed that the amounts of active released after 1, 2, and 3 hours were 55%, 69%, and 74%, respectively.

Comparative Example A

Comparative tablets were prepared from the following dry composition: 45% Avicel® PH-102, 40% Eudragit®-coated theophylline, 10% starch 1500, and 5% croscarmellose sodium using the same tableting procedure and conditions as for Example 1. Under the same conditions as Example 1 after 1, 2, and 3 hours, the release of theophylline was 60%, 86%, and 98%, respectively. The increased release rates of the tablets of Comparative Example A, as compared to the release rates of the tablets of Example 1 is an indication that the sustained release particles of the tablets of Comparative Example A sustained more damage during tableting than the sustained release particles of the tablets of Example 1.

EXAMPLE 2

In a Hobart mixer was placed 500 grams of Avicel® PH-102 (average particle size—100 microns). To this mixer was then added a mixture of 300 grams of deionized water and 300 grams of isopropyl alcohol. Mixing continued until an evenly wet granulation had formed. This wet mass was passed through a Fitz-Mill, Model M, fitted with a 12 mesh (1680 microns) screen, running at 1000 rpm. The MCC granules were placed on a lined tray and dried for approximately sixteen hours at ambient temperature. Drying was completed by placing the MCC granules in an oven at 80° C. for a two-hour period. A second identical formulation was prepared using the identical process. After both batches were fully dried, they were combined. The particle size distribution of the combined batches was determined using a tower of screens in which each successive screen had a finer mesh than the screen above it. The particle size distribution was: 20 mesh (>840 microns), 27.7%; 30 mesh (840–590 microns), 15.3%; 40 mesh (590–420 microns), 16.4%; 50 mesh (420–297 microns), 13.2%; 60 mesh (297–250 microns), 6.5%; 100 mesh (250–149 microns), 14.3%; and <100 mesh (<149 microns), 6.9%. The mean particle size was determined to be 550 microns. The tapped bulk density was determined to be 0.3247 grams/cc. A dry composition was prepared in which 12.5% by weight of Eudragit®-coated theophylline spheres and 87.5% by weight of the MCC granules made by the procedure given above were intimately mixed. This mixture was tableted using 15.88 mm (0.625 inch) flat faced, bevel-edged tooling at a compression force of 164 Kg.

The hardness of the resulting tablets was 2.2 Kp, and their friability was 2.12%. The release of theophylline, using the procedure described in Example 1 except that the solution was replaced with 900 ml of 0.05 M phosphate buffer at pH 3.0 with 0.12 M chloride ion, was 8% after one hour and increased to 25% after 3.5 hours.

By comparison, the release rates for uncompressed theophylline-containing sustained release particles were measured using the same procedure of Example 2 and found to be 8% at 1 hour and 31% at 3.5 hours.

Comparative Examples B–C

In a Hobart mixing bowl was placed 5 Kg of Avicel® PH-101. A mixture of 4.9 Kg of purified water and 2.1 Kg of 99.9% isopropyl alcohol was prepared and added to the granulator bowl with continuous mixing during a period of about two minutes. Mixing was continued for 25 minutes after addition of the granulating fluid was complete. At the end of this period the MCC granules were passed through an 18 mesh (1000 micron) screen and deposited on trays which were then placed in a 50° C. oven to dry overnight. Eudragit®-coated theophylline spheres (150 grams) and 6 grams of colloidal silicon dioxide were placed in a stainless steel twin shell blender and mixed for 5 minutes. To the blender was then added 450 grams of dry MCC granules, and mixing was continued for an additional 10 minutes. This formulation was compressed on a Stokes 512 tablet press using 12.7 mm (0.5 inch) round flat-faced, bevel-edged tooling at a compression force of 554 Kg. The resulting tablets had a hardness of 1.1 Kp and a friability of 100%. Another set of tablets was prepared at a compression force of 989 Kg. These tablets had a hardness of 2.5 Kp and a friability of 32.7%. The MCC granules of both sets of tablets were found to be too dense to provide adequate cushioning properties. The high density may have been due to one or more of the use of an excessive amount of granulating fluid and/or water in the granulating fluid, over-mixing during the granulation and the oven drying step.

EXAMPLES 3–4

Two additional sets of tablets were prepared using the same procedure as for Comparative Examples B–C except that the amounts of the ingredients were changed as indicated in Table 1 and the compression force used in tableting was varied as shown in Table 2.

The release rate of theophylline from these tablets was determined by the method described in Example 1, except that the solution was replaced with 900 ml of 0.05 M phosphate buffer at pH 3.0 with 0.12 M chloride ion. Table 1 summarizes the quantities of material used in each granulation and the properties of the MCC granules produced. Table 2 summarizes the properties of the Eudragit®-coated, theophylline-containing tablets prepared at two different compression forces.

TABLE 1

Granulation Parameters and Physical Properties

| Example | B–C | 3–4 |
|---|---|---|
| Water/IPA[a] | 70/30 | 30/70 |
| % Fluid[b] | 140 | 100 |
| Mixing Time (min) | 25 | 5 |
| Screen (μm) | 1000 | 1680 |

| Mesh Size | Particle Size Distribution Particle Size (μm) | Examples B–C % Retained | Examples 3–4 % Retained |
|---|---|---|---|
| 20 | 840 | 1.8 | 10.1 |
| 30 | 590 | 10.5 | 11.8 |
| 40 | 420 | 14.5 | 11.3 |
| 50 | 297 | 16.9 | 13.6 |
| 60 | 250 | 6.3 | 6.4 |
| 100 | 149 | 20.0 | 23.1 |
| <100 | <149 | 29.9 | 23.7 |
| Loose Bulk density (g/cc) | | 0.566 | .0349 |

[a]IPA = 99.9% isopropyl alcohol
[b]Amount of granulating fluid as a percentage of the solid MCC content (Avicel® PH-101)
[c]Mixing time for the MCC and the granulating fluid prior to being passed through the screen

TABLE 2

Tableting and Release Properties

| | Example | | Uncompressed Sustained Release |
|---|---|---|---|
| | 3 | 4 | Particles |
| Compression Force (Kg) | 561 | 1001 | N/A |
| Hardness (Kp) | 4.1 | 10.4 | N/A |
| Friability (%) | 0.1 | 0.0 | N/A |
| Release (%) at | | | |
| 1 hour | 22 | 21 | 8 |
| 3.5 hours | 55 | 55 | 31 |

EXAMPLES 5–6

500 g of MCC granules prepared by the granulation process of the present invention using a granulating fluid containing a mixture of water and a water-miscible polar organic solvent were dry blended with 89 g of polyvinyl pyrrolidone (PVP K25) in a fluid bed processor. Using a top spray configuration, 312.4 grams of deionized water was applied to the blended materials at an inlet temperature of 60° C. and an outlet temperature of 20–24° C. using a spray pressure of 0.5 bar at a spray rate of 10 g/min using a variable air flow rate. The air flow rate was adjusted to provide the least amount of air flow which still fluidized the materials in the fluid bed.

After all of the materials were wet out, the MCC granules containing-hydrocolloid were oven dried at 80° C. for 1.5 hours to remove any remaining deionized water. The MCC granules containing hydrocolloid were then screened through a 16 mesh screen.

Cushioning MCC granules containing hydrocolloid made by this process were used as is (Example 5) or further conditioned at 85% relative humidity (RH) until equilibrium (Example 6).

The cushioning material physical properties for Examples 5–6 are given in Table 3. The properties of tablets made with the MCC granules of Examples 5–6 are given in Table 4.

EXAMPLES 7–8

89 g of polyvinyl pyrrolidone (PVP K25) were dissolved in 312.4 g of deionized water. 500 g of MCC granules prepared by the granulation process of the present invention using a granulating fluid containing a mixture of water and a water-miscible polar organic solvent were placed in a fluid bed processor. Using a top spray configuration the solution of PVP in water is applied to the MCC granules at an inlet temperature of 60° C. and an outlet temperature of 20–23° C. using a spray pressure of 0.5 bar at a spray rate of 18 g/m using a variable air flow rate. The air flow rate was adjusted to provide the least amount of air flow which still fluidized the materials in the fluid bed.

After the MCC granules are wet out and granulated, the MCC granules containing hydrocolloid were oven dry at 80° C. for 1.5 hours and screened through a 16 mesh screen.

Cushioning MCC granules containing hydrocolloid made by this process were used as is (Example 7) or further conditioned at 85% RH until equilibrium (Example 8).

The cushioning material physical properties for Examples 5–6 are given in Table 3. The properties of tablets made with the MCC granules of Examples 5–6 are given in Table 4.

TABLE 3

Cushioning Material Physical Properties

Moisture-

| | |
|---|---|
| Control example (MCC granules without PVP addition) | 4.994% |
| Control example (conditioned at 85% RH) | 8.208% |
| Example 5 | 2.869% |
| Example 6 (conditioned at 85% RH) | 9.983% |
| Example 7 | 1.523% |
| Example 8 (conditioned at 85% RH) | 10.940% |

Loose Bulk Density-

| | |
|---|---|
| Control example (MCC granules without PVP Processing) | 0.3608 g/cc |
| Example 5 | 0.3412 g/cc |
| Example 7 | 0.3568 g/cc |

Particle Size Distribution-

| Mesh Size | Particle Size (μm) | Control | Example 5 | Example 7 |
|---|---|---|---|---|
| 20 mesh | 840 | 0.0% | 4.0% | 0.2% |
| 30 mesh | 590 | 2.0% | 6.0% | 2.0% |
| 40 mesh | 420 | 4.0% | 36.0% | 3.4% |
| 50 mesh | 297 | 6.0% | 20.0% | 6.0% |
| 60 mesh | 250 | 4.0% | 8.0% | 3.2% |
| 80 mesh | 177 | 64.0% | 16.0% | 65.2% |
| <80 | <177 | 20.0% | 10.0% | 20.0% |

EXAMPLE 9

Tableting of the MCC Granules of Examples 5–8

All cushioning materials of Examples 5–8 were blended in the following formulation for tablet evaluation. Tablets were compressed to yield friability below 2.0% and compressed at different compression forces (CF) as indicated below. A capsule-shaped FMC logo tooling was used. The tablet formulates contained the following ingredients:

| | |
|---|---|
| Coated Theophylline Sphere | 25.0% |
| Cushioning Materials | 74.0% |
| Ac-Di-Sol | 1.0% |
| Total Tablet Weight | 587.2 mg |

Dissolution data for these tablets are given in Table 4.

TABLE 4

Dissolution Data

| | | |
|---|---|---|
| Uncompressed Spheres Unconditioned Batches: | At 1 hr 8% ± 0.6% | At 3.5 hrs 31% ± 2.5% |
| Control - CF of 350 kg | At 1 hr 22% ± 0.6% | At 3.5 hrs 56% ± 3.1% |
| Control - CF of 550 kg | At 1 hr 24% ± 4.7% | At 3.5 hrs 58% ± 8.4% |
| Example 5 - CF of 560 kg | At 1 hr 17% ± 3.2% | At 3.5 hrs 47% ± 4.7% |
| Example 5 - CF of 700 kg | At 1 hr 22% ± 1.0% | At 3.5 hrs 59% ± 2.6% |
| Example 7 - CF of 570 kg | At 1 hr 9% ± 1.5% | At 3.5 hrs 27% ± 4.6% |
| Example 7 - CF of 700 kg | At 1 hr 14% ± 0.0% | At 3.5 hrs 43% ± 1.0% |
| Conditioned Batches (85% RH to equilibrium): | | |
| Control - CF of 350 kg | At 1 hr 18% ± 1.5% | At 3.5 hrs 44% ± 3.1% |
| Control - CF of 550 kg | At 1 hr 24% ± 1.7% | At 3.5 hrs 56% ± 3.5% |
| Example 6 - CF of 350 kg | At 1 hr 12% ± 0.6% | At 3.5 hrs 36% ± 1.5% |
| Example 6 - CF of 560 kg | At 1 hr 10% ± 1.2% | At 3.5 hrs 28% ± 0.6% |
| Example 8 - CF of 350 kg | At 1 hr 16% ± 1.0% | At 3.5 hrs 38% ± 1.2% |
| Example 8 - CF of 560 kg | At 1 hr 21% ± 0.6% | At 3.5 hrs 47% ± 0.6% |

The foregoing examples were presented for the purpose of illustration and description only and are not to be construed as limiting the invention in any way. The scope of the invention is to be determined from the claims appended hereto.

We claim:

1. A method for preparing porous microcrystalline cellulose granules comprising the following steps:
    (a) granulating microcrystalline cellulose with a granulating fluid comprising water and a water-miscible, volatile, polar organic solvent to provide a granulated microcrystalline cellulose;
    (b) drying the granulated microcrystalline cellulose at a controlled rate with no heat input at ambient temperature for a time sufficient to remove at least substantially all of the polar organic solvent from the granulated microcrystalline cellulose without removing at least a substantial portion of the water from the granulated microcrystalline cellulose, and without extruding or spheronizing the granulated microcrystalline cellulose from granulation step (a); and
    (c) subsequent to step (b), removing at least a substantial portion of the water from the granulated microcrystalline cellulose.

2. The method of claim 1 wherein said polar organic solvent is selected from the group consisting of methanol, ethanol, propanol, isopropanol, t-butyl alcohol and acetone.

3. The method of claim 2 wherein said polar organic solvent is isopropanol.

4. The method of claim 1 wherein the volume ratio of water to said polar organic solvent in said granulating fluid is from 85:15 to 15:85.

5. The method of claim 1 wherein the ratio of said granulating fluid to said microcrystalline cellulose in the granulating step is from 1:2 to 2:1.

6. The method of claim 1 wherein said granulated microcrystalline cellulose is initially dried at controlled temperature and pressure and once substantially all of the polar organic solvent is removed, further drying is carried out at one or more of an elevated temperature, reduced pressure or both.

7. The method of claim 1 further comprising the step of adding to the granulated microcrystalline cellulose about 1 to about 30% by weight of a hydrocolloid, based on the weight of the granulated microcrystalline cellulose.

8. The method of claim 7 wherein the hydrocolloid is added to the granulated microcrystalline cellulose prior to the drying step which removes substantially all of the polar organic solvent component from the granulated microcrystalline cellulose.

9. The method of claim 7 wherein the hydrocolloid is added to the microcrystalline cellulose granules after substantially all of the polar organic solvent has been removed from the granulated microcrystalline cellulose.

10. The method of claim 7 wherein in the adding step the hydrocolloid is coated onto the surface of the microcrystalline cellulose granules.

11. The method of claim 7 wherein the hydrocolloid comprises one or more hydrocolloids selected from the group consisting of: methylcellulose, hydroxypropyl cellulose, sodium carboxymethylcellulose, hydroxypropyl methylcellulose, gelatin, water soluble cellulose acetate, polyvinyl pyrrolidone, starches, alginates, alginic acid, locust bean seed extract, guar seed extract, carrageenan, gum tragacanth, gum arabic and gum karoya.

12. The method of claim 11 wherein the hydrocolloid is selected from the group consisting of polyvinyl pyrrolidone, methylcellulose, hydroxypropyl cellulose and hydroxypropyl methylcellulose.

13. The method of claim 11 wherein the hydrocolloid comprises polyvinyl pyrrolidone.

14. Porous, granulated microcrystalline cellulose made by the process of claim 7 having a loose bulk density of from about 0.2 g/cc to about 0.4 g/cc, and a mean particle size of from about 250 microns to about 1500 microns.

15. Porous, granulated microcrystalline cellulose made by the process of claim 1 having a loose bulk density of from about 0.2 g/cc to about 0.4 g/cc, and a mean particle size of from about 250 microns to about 1500 microns.

16. Porous microcrystalline cellulose granules having an irregular shape, a loose bulk density of from about 0.2 g/cc to about 0.4 g/cc, and a mean particle size of from about 250 microns to about 1500 microns.

17. Microcrystalline cellulose granules as claimed in claim 16 having a loose bulk density of from about 0.25 to about 0.35 g/cc.

18. Microcrystalline cellulose granules as claimed in claim 16 having a mean particle size of from about 250 microns to about 1000 microns.

19. Microcrystalline cellulose granules as claimed in claim 16 having a mean particle size of from about 400 microns to about 900 microns.

20. Microcrystalline cellulose granules as claimed in claim 16 further comprising from about 1% to about 30% by weight, of a hydrocolloid, based on the weight of the granulated microcrystalline cellulose.

21. Microcrystalline cellulose granules as claimed in claim 20 wherein the hydrocolloid comprises one or more hydrocolloids selected from the group consisting of: methylcellulose, hydroxypropyl cellulose, sodium carboxymethylcellulose, hydroxypropyl methylcellulose, gelatin, water soluble cellulose acetate, polyvinyl pyrrolidone, starches, alginates, alginic acid, locust bean seed extract, guar seed extract, carrageenan, gum tragacanth, gum arabic and gum karoya.

22. Microcrystalline cellulose granules as claimed in claim 21 wherein the hydrocolloid is selected from the group consisting of polyvinyl pyrrolidone, methylcellulose, hydroxypropyl cellulose and hydroxypropyl methylcellulose.

23. Microcrystalline cellulose granules as claimed in claim 21 wherein the hydrocolloid comprises polyvinyl pyrrolidone.

24. A tablet which comprises from about 5% to about 80% by weight of granulated microcrystalline cellulose as claimed in claim 23; from about 5% to about 80% by weight of one or more controlled release particles and barrier coated materials which contain an active ingredient; and 0% to about 20% by weight of other excipients, based on the total weight of the tablet.

25. A tablet which comprises from about 5% to about 80% by weight of granulated microcrystalline cellulose as claimed in claim 20; from about 5% to about 80% by weight of one or more of controlled release particles and barrier coated materials which contain an active ingredient; and 0% to about 20% by weight of other excipients, based on the total weight of the tablet.

26. A tablet which comprises from about 5% to about 80% by weight of granulated microcrystalline cellulose as claimed in claim 16; from about 5% to about 80% by weight of one or more of controlled release particles and barrier coated materials which contain an active ingredient; and from 0% to about 20% by weight of other excipients, based on the total weight of the tablet.

* * * * *

UNITED STATES PATENT AND TRADEMARK OFFICE
CERTIFICATE OF CORRECTION

PATENT NO. : 6,858,725 B1
DATED : February 22, 2005
INVENTOR(S) : Ronald S. Vladyka, Jr.

It is certified that error appears in the above-identified patent and that said Letters Patent is hereby corrected as shown below:

Title page,
Insert Item -- [62], Related Application Data,
This application claims the benefit of U.S. Provisional Patent Application
No. 60/165,121, filed November 12, 1999, under 35 U.S.C. sec. 119(e). --.

Signed and Sealed this

Fourteenth Day of February, 2006

JON W. DUDAS
*Director of the United States Patent and Trademark Office*